United States Patent [19]

Magrath

[11] Patent Number: 4,752,291
[45] Date of Patent: Jun. 21, 1988

[54] ADAPTER FOR CONNECTING MEDICAMENT SUPPLY AND APPLICATOR

[76] Inventor: Joseph M. Magrath, Box 148, McCook, Nebr. 69001

[21] Appl. No.: 9,910

[22] Filed: Feb. 2, 1987

[51] Int. Cl.⁴ .......................................... A61M 5/325
[52] U.S. Cl. .................................... 604/240; 604/241
[58] Field of Search ...................... 604/240, 241, 275

[56] References Cited

U.S. PATENT DOCUMENTS

| | | | |
|---|---|---|---|
| 2,186,711 | 1/1940 | Schleicher | 604/275 |
| 2,734,665 | 2/1956 | Flamm | 604/275 X |
| 3,322,101 | 5/1967 | Eagles et al. | 604/275 X |
| 3,402,714 | 9/1968 | Higgins et al. | 604/241 |

Primary Examiner—John D. Yasko
Attorney, Agent, or Firm—Wm. Griffith Edwards

[57] ABSTRACT

An equipment for supplying veterinary medicament from a supply tube to an applicator comprises a generally cylindrical body having a passage therethrough including a large chamber for receiving the discharge end of a supply tube and a communicating passage of smaller diameter to receive the nozzle of the supply tube. The body is made of a hard synthetic plastic, and internal threads near the discharge end of the smaller passage are arranged to engage the nozzle and when it is turned cut threads thereon and hold the nozzle securely in position in the adapter. The adapter may be used repeatedly with successive supply tubes.

5 Claims, 2 Drawing Sheets

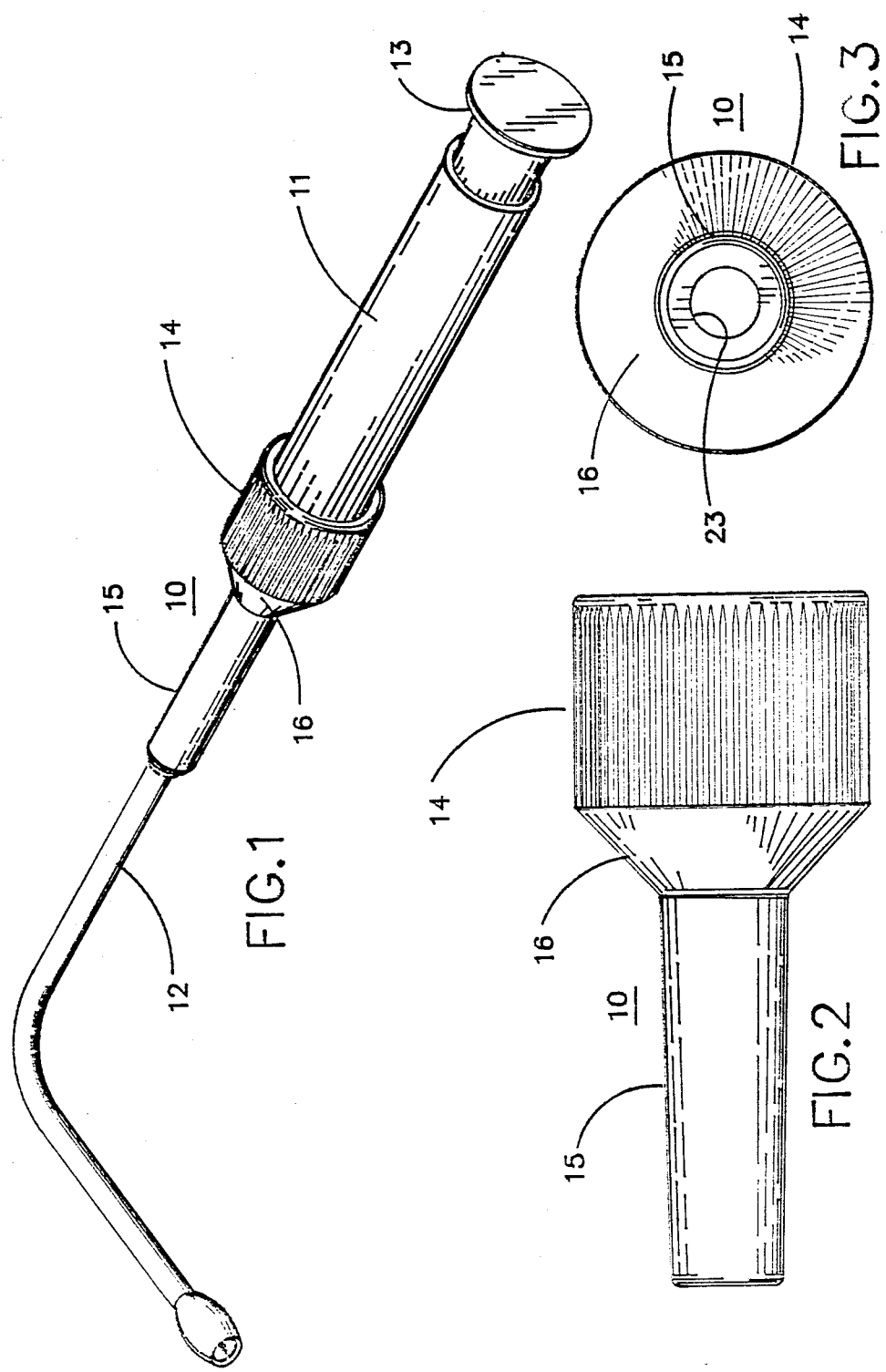

ADAPTER FOR CONNECTING MEDICAMENT SUPPLY AND APPLICATOR

This invention relates to an adapter which is particularly useful in the field of veterinary medicine for the purpose of connecting a medicament supply tube and an applicator for supplying the medicament to an animal.

Various forms of applicators are provided for supplying medicaments to animals and for many applications it is desirable to provide an arrangement for applying a medicament to the oral cavity of the animal while the operator is positioned rearwardly of the animal's head. A hooked applicator tube may be employed for this purpose. The medicament is supplied in tubes which may be discharged by operating a plunger therein or by applying air pressure to a piston therein and in some cases the application is effected by compressing the supply tube.

It is an object of the present invention to provide a reliable and simplified arrangement for supplying medicament from a supply tube to an applicator and for minimizing the difficulty in supplying the medicament to the animal.

It is another object of this invention to provide an improved adapter for connecting a medicament supply tube and an applicator device.

BRIEF SUMMARY OF THE DISCLOSURE

A flow connecting adapter is provided for connecting a medicament supply tube and an applicator; the adapter is constructed of rigid synthetic plastic material. The adapter is provided with a cylindrical portion which fits about the end of the supply tube and over the tube nozzle; the adapter is so arranged that it may be screwed onto the end of the nozzle, thereby securing it to the supply tube. The applicator is also attached to the adapter by internal threads at the other end from the supply tube, so that when fluid materials are discharged from the supply tube they pass through the adapter into the applicator and hence to the animal's oral cavity. The adapter may be used repeatedly and greatly simplifies the operation of supplying fluid medicaments to animals to be treated.

BRIEF DESCRIPTION OF THE DRAWINGS

FIG. 1 is an isometric view of an adapter shown in position on a supply tube and connected to an applicator;

FIG. 2 is a side elevation view of the adapter;

FIG. 3 is a left hand end view of the adapter;

DETAILED DESCRIPTION OF THE DRAWINGS

Figure 4:
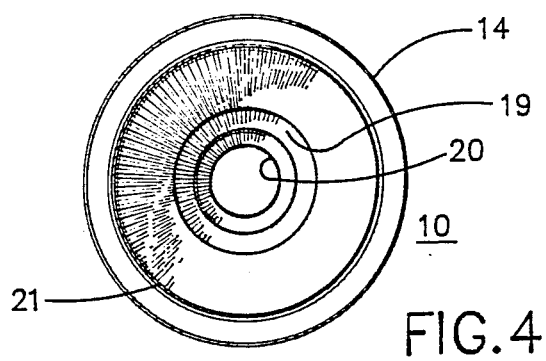
FIG. 4 is a right hand end view of the adapter.

Referring to the drawings, as shown in FIG. 1, an adapter 10 is fitted on a medicament supply tube 11 and has an applicator 12 connected at its other end to receive medicament from the adapter. The supply tube 11 may be of any suitable type available on the market, and has been illustrated as having a handle 13 which may be drawn longitudinally away from the tube body, and then pressed forward to discharge the medicament through the adapter 10 and into the applicator 12. Other types of supply tubes are actuated by air pressure applied to the piston, and some are collapsible tubes which may be discharged by hand pressure upon squeezing the tube wall. The adapter 10 which is preferably made of a hard synthetic plastic provides a convenient handle for holding the tube and for placing the applicator in an animal's oral cavity for the discharge of the medicament. The hook shaped applicator, as illustrated, is particularly suited for supplying a medicament to animals such as calves. For this purpose the person giving the treatment stands at the side of the animal, rearwardly of the head, and holds the adapter in position with the discharge end of the hook shaped applicator in the oral cavity while applying pressure on the supply tube with the other hand.

The adapter may be used repeatedly with successive supply tubes, and is easily cleaned and maintained ready for use.

The details of construction of the adapter are shown in FIGS. 2 through 5.

As shown in FIG. 2 the adapter 10 comprises a cylindrical section 14 and an elongated generally cylindrical section 15 of smaller diameter, the two sections being connected by a conical section 16. FIG. 3 which is the left end view shows the circular configuration of the adapter and an opening 17 having threads 18 which are provided to receive the threaded end connection of an applicator, the opening 17 being the passage through which the medicament flows from the adapter to the applicator.

FIG. 4 which is a right hand end view of the adapter shows the opening through which the supply tube is inserted and indicates the sloping wall 16 and an internal sloping wall 19 which connects the interior of the wall 16 and the reduced passageway of the adapter. Threads 20 project into the passageway for engagement with the nozzle of a supply tube which can be screwed into position thereon and thereby be retained in the adapter. The details are more clearly shown in FIG. 5 which is the longitudinal sectional view of the adapter.

Figure 5:
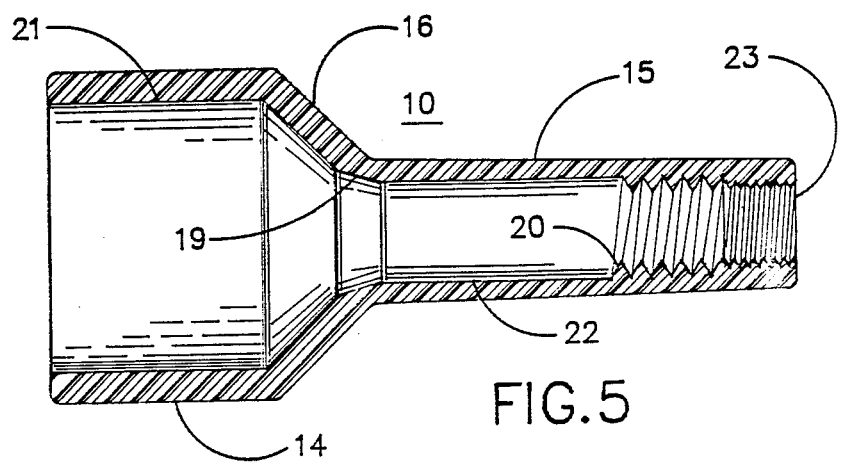
FIG. 5 is a longitudinal sectional elevation view of the adapter.

Referring now to FIG. 5 the main cylindrical chamber for holding the supply tube is indicated at 21 and the elongated passage for the nozzle of the supply tube is indicated at 22. The walls of these two generally cylindrical chambers are connected by the sloping wall 16 and the less sloping wall 19. The configuration of the overall chamber thus formed holds the supply tube in place and accomodates irregularities between tubes from different sources. The portion of the adapter in which the elongated passage is located terminates in an internally threaded portion including the threads 20 for securing the nozzle of the supply tube and a second threaded portion 23 which is threaded to receive the threaded end of the applicator tube. The threads 20 while of essentially the same diameter are somewhat different from the threads 23, being somewhat larger and sharpened to receive the nozzle and hold the supply tube in position in the adapter. The threads 20 are made of a size and arranged to receive nozzles within a range of sizes and to hold them securely in place. Threads 23 are, of course, made to accomodate and securely hold the threaded end of the applicator tube.

Figure 6:
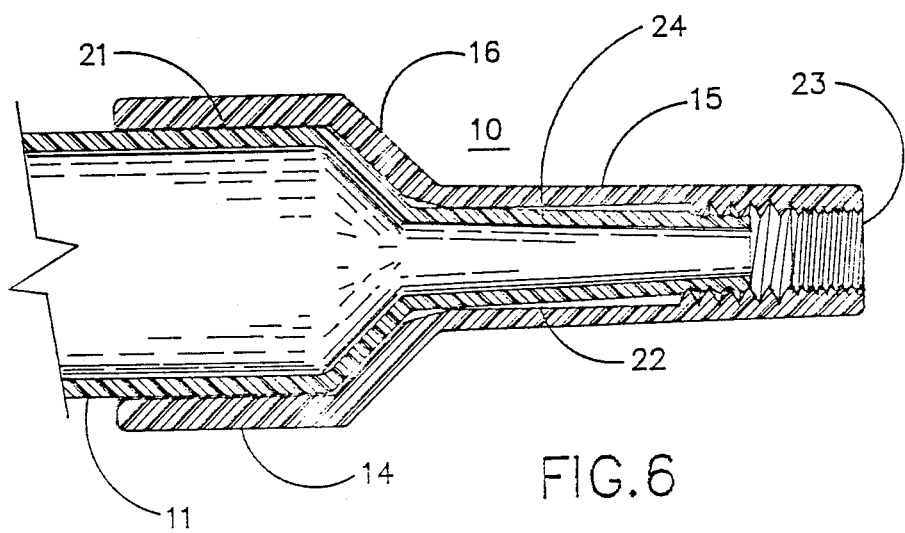
FIG. 6 is a sectional view similar to FIG. 5 showing a supply tube nozzle in place.

When the adapter is to be used, a full supply tube is placed in the chamber 21 with its nozzle 24 extending into the chamber 22 and the nozzle of the tube is placed in position resting against the first turn of the threads 20. The adapter is then turned until it engages the threads 20 and the threads operate to cut threads in the nozzle and hold the nozzle in place drawing it tightly against the adapter so that usually the wall of the tube will lie against the wall 16 of the adapter as shown in FIG. 6. When the applicator has been positioned on the outer end of the adapter the combined unit is ready for use. The applicator is then placed in the oral cavity of the animal and while it is held in position medicament is discharged through the applicator tube. The adapter makes it easy to handle the supply tube and applicator and makes it possible to apply the medicine with less disturbance to the animal.

After the adapter has been used, the applicator and supply tube are removed and the adapter is cleaned and ready for the next use.

While the invention has been described in connection with a specific modification other modifications and applications will occur to those skilled in the art, therefore, it is not desired that the invention be limited to the details illustrated and described and it is intended by the appended claims to cover all modifications which fall within the spirit and scope of the invention.

I claim:

1. As an article of manufacture an adapter for connecting a treating applicator to a medicament supply tube which tube has an elongated discharge nozzle as an integral part thereof, said adapter being hollow and of a generally cylindrical configuration with an internal passage for receiving the end of the supply tube and a smaller passage extending axially therefrom for receiving the discharge nozzle of the supply tube, internal threads on the wall of said smaller passage for receiving the end of the discharge nozzle whereby the nozzle may be screwed into position in said smaller passage, the nozzle engaging said internal threads and being threaded as it is screwed into position, the supply tube being secured in position thereby, and means for attaching an applicator to said adapter in communication with said smaller passage for directing the flow of medicament discharge from the supply tube.

2. An adapter as set forth in claim 1 wherein said adapter is made of a hard material substantially harder than that of the nozzle of the supply.

3. An adapter as set forth in claim 2 wherein the hard material is a synthetic plastic.

4. An adapter as set forth in claim 1 wherein the wall of the internal passage in said adapter includes an abruptly forwardly sloping portion between said supply tube passage and said smaller passage.

5. An adapter as set forth in claim 2 wherein said applicator attaching means comprises additional threads on the walls of said smaller passage between said internal threads and the open end of said smaller passage.

* * * * *